(12) United States Patent
Basagañas Millan

(10) Patent No.: US 6,278,840 B1
(45) Date of Patent: Aug. 21, 2001

(54) EVAPORATOR DEVICE OF VOLATILE PRODUCTS WITH VARIABLE EVAPORATION INTENSITY

(75) Inventor: Jordi Basagañas Millan, Cerdanyola del Vallés (ES)

(73) Assignee: DBK Espana, S.A., Cerdanyola del Vallas (ES)

( * ) Notice: Subject to any disclaimer, the term of this patent is extended or adjusted under 35 U.S.C. 154(b) by 0 days.

(21) Appl. No.: 09/446,720

(22) PCT Filed: Jun. 23, 1998

(86) PCT No.: PCT/EP98/04010
§ 371 Date: Dec. 22, 1999
§ 102(e) Date: Dec. 22, 1999

(87) PCT Pub. No.: WO98/58692
PCT Pub. Date: Dec. 30, 1998

(30) Foreign Application Priority Data

Jun. 24, 1997 (ES) .................................................... 9701388

(51) Int. Cl.[7] ............................... A61M 16/00; F24F 6/08
(52) U.S. Cl. .................. 392/390; 392/395; 261/DIG. 65
(58) Field of Search .................................... 392/386, 390, 392/392, 394, 395; 261/139, 142, 99, DIG. 65; 215/44, 50, 201, 215, 217, 218

(56) References Cited

U.S. PATENT DOCUMENTS 3,966,082 * 6/1976 Hopkins ................................ 215/225
4,032,028 * 6/1977 Reiss et al. .......................... 215/217
4,298,129 * 11/1981 Stull ..................................... 215/217
5,038,394 * 8/1991 Hasegawa et al. ................... 392/395
5,222,186 * 6/1993 Schimanski et al. ................ 392/395

FOREIGN PATENT DOCUMENTS

| 0362397 | 4/1990 | (EP). |
| 0420144 | 4/1991 | (EP). |
| 0736248 | 10/1996 | (EP). |
| 2194442 | 3/1988 | (GB). |
| 9819526 | 5/1998 | (WO). |

* cited by examiner

*Primary Examiner*—Sang Paik

(57) ABSTRACT

The adjustment of the intensity of evaporation is conducted by means of the variation in the relative position between the upper end (6') of the wick (6) which absorbs the product of the vessel (2) and the electroheating resistors (5) which favour the evaporation of said product, and more specifically keeping static said resistors and the assembly constituted by the vessel (2) and the wick (6) being displaceable. For this, said vessel (2) with any configuration, is provided with at least one revolution sector (7) in which a helicoidal groove (8) is established, of great pitch, operating as thread for the axial displacement of the container (2), when a rotational movement is applied to the same, at least one pair of opposed teeth (9) collaborating with said groove (8) which are finished off with leastically deformable arms (10) of the casing (1).

18 Claims, 5 Drawing Sheets

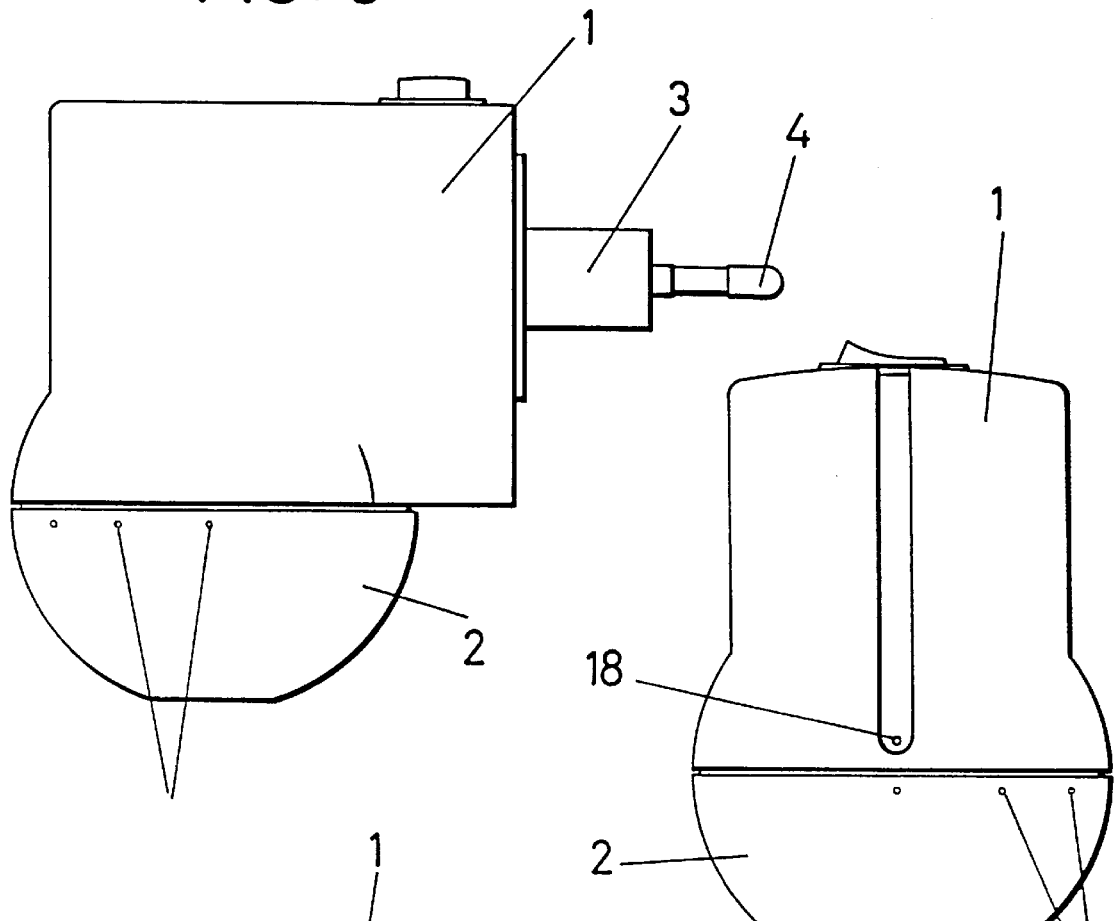
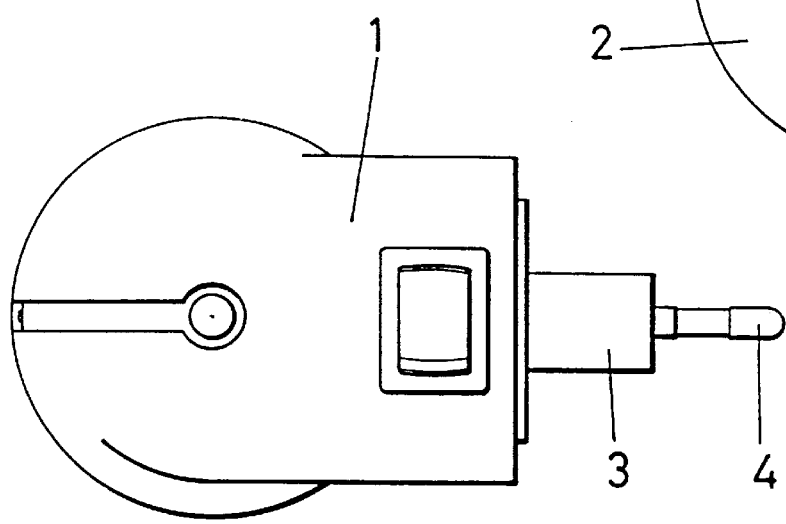

A-B

EVAPORATOR DEVICE OF VOLATILE PRODUCTS WITH VARIABLE EVAPORATION INTENSITY

OBJECT OF THE INVENTION

The present invention refers to an evaporator device of volatile products, be they environmental products or insecticide products, of the type which use electroheating resistors to improve the evaporation or volatilization of the product, and of those which use a wick which absorbs said product from the corresponding container vessel up to the area of influence of the electroheating resistor.

BACKGROUND OF THE INVENTION

Evaporators of volatile products which are provided with a vessel in which the product in question is housed are well known, whether dealing with an environmental product or with an environmental insecticide, a wick being extended between the bottom of said vessel and the electroheating resistor through which said product rises to reach the area of influence of the resistor.

In this type of devices and as is obvious, the intensity of the evaporation or diffusion of the product is constant, whilst product exists in the container vessel.

However, in practice, it may be desirable to decrease or increase as desired, in specific moments, the intensity of the environmental supply of the product. In this sense, a solution is known which is included in Utility Model 9002819, according to which, the electroheating resistor is assembled with floating nature in the centre of the device, in such a manner, that by means of guides and of a manual activating mechanism, it is capable of moving axially, varying its level of confrontation to the upper end of the wick and, consequently, varying its effectiveness as heating element and a level of diffusion of the product.

However, this solution results to be structurally complex since it requires a resistor assembled on a special support, moveable, which must be related to the plug socket through flexible cables, which permit its axial movement, all of which, increases the difficulty and makes its constructive process expensive.

DESCRIPTION OF THE INVENTION

The device proposed by the invention solves in a totally satisfactory manner the previously indicated problem, based on a completely different concept, specifically based in maintaining static the electroheating resistor and to achieve the displacement of the vessel, and consequently the wick which is associated to the same.

More specifically, it has been provided, that said vessel presents at least one revolution sector in which a helicoidal groove is established which determines a large pitch thread, whilst in the casing of the device, holder of unmoveable nature of the electroheating resistor, at least one pair of opposed teeth are established, functioning as complementary threads, which determine, for the container vessel, an accused axial displacement, when a rotational movement is administered to the same.

According to another of the characteristics of the invention, said helicoidal groove of the vessel may present closed ends, in such a manner that they constitute rotation restricting stops in one and another direction, which establish the two limit positions of the maximum and minimum intensity of evaporation, at the same time that said opposed attachment and displacement teeth of the vessel as regards the casing, are assembled on elastically deformable arms which, with a specific effort, permit the assembly and disassembly of said vessel when it is necessary to replace the same. However, said rotation restricting stops may be obtained by other means, such as for example, by means of a hook acting on a lip of the vessel Given that the container vessel is generally constructed into a bottle provided with a screw stopper for a sealed closure during the storage prior to its consumption, it has been foreseen that, optionally, it may be the actual thread corresponding to the stopper of the container, which replaces the previously indicated helicoidal groove, coupling the teeth of the casing to said thread, in which case, the same effect is obtained as in the previous case, though with a slower axial movement, which requires a wider rotational movement, requiring the existence of complementary means to prevent the total accidental uncoupling of the vessel as regards the casing. It is also possible that the helicoidal large pitch groove shall be superposed on the actual thread of the stopper.

In any case, it is achieved that as from a fixed casing in which a resistor or set of also fixed electroheating resistors are established, the intensity of evaporation can be adjusted as desired, with only the supplying of a rotational movement to the container vessel of the product, which additionally is more easily coupled and uncoupled in the centre of said casing.

According to another of the characteristics of the invention it has been provided that the device include indicating means of the level of intensity of evaporation, which act depending on the relative position between the casing of the device and the body of the container, either detecting the axial position of the latter, or else its angular positioning, in any case, as regards the fixed casing.

DESCRIPTION OF THE DRAWINGS

To complement the description which is being made, and with the object of helping to a better understanding of the characteristics of the invention, according to a preferred exemplary practical embodiment of the same, a set of drawings is enclosed, forming integral part of said description, in which, with illustrative and non limitative character, the following has been represented:

FIG. 3 shows a side elevational view of the device of the previous figures, opposed to that of FIG. 1 and with the casing without being sectioned.

FIG. 4 shows in turn, a side elevational view which is similar to that of FIG. 2 though also with the casing without being sectioned.

FIG. 5 shows a plan view of the assembly represented in FIGS. 3 and 4.

PREFERRED EMBODIMENT of THE INVENTION

Figure 1:
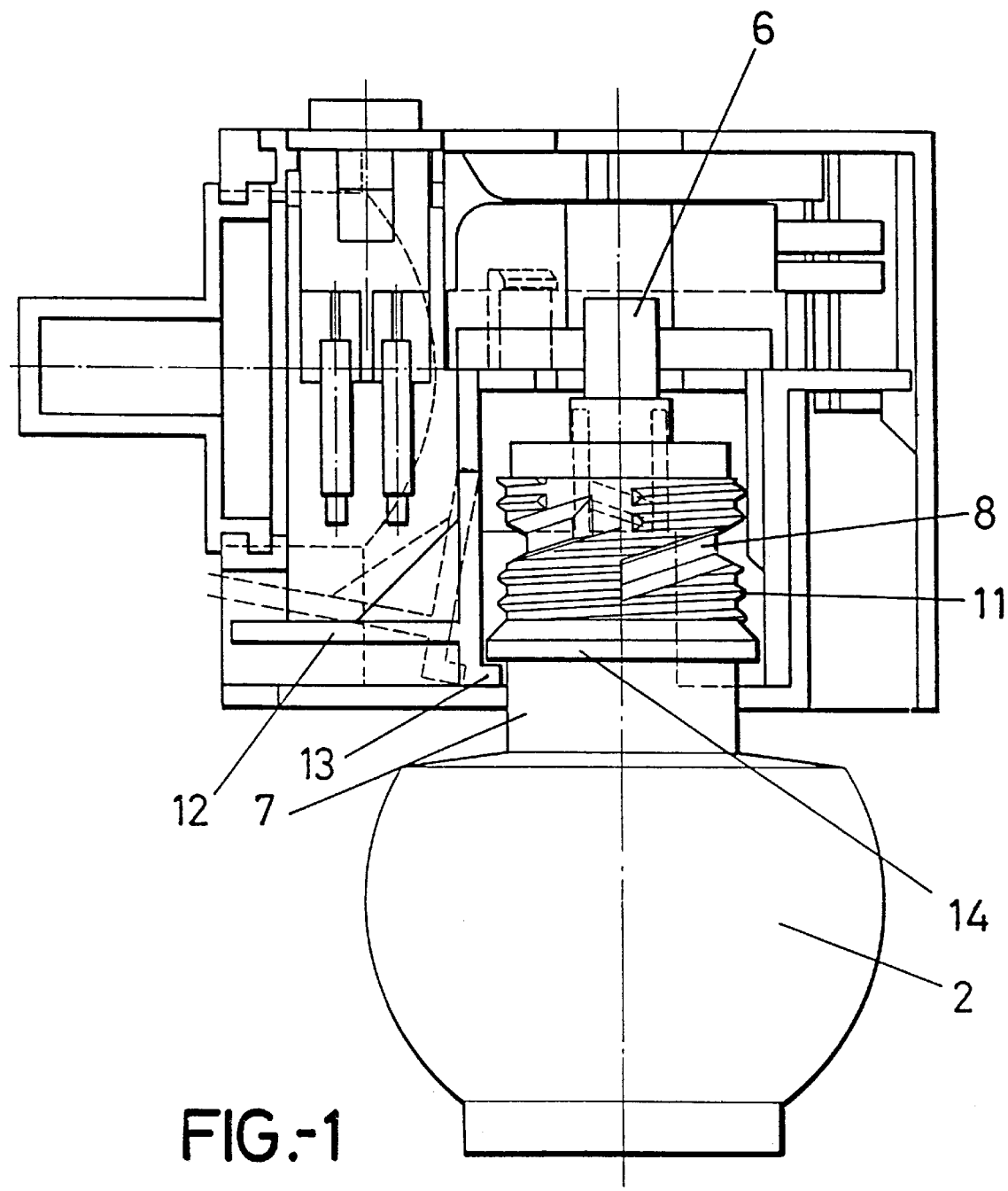
FIG. 1 shows an exploded, side elevational representation of an evaporator device of volatile products with variable evaporation intensity embodied according to the object of the present invention, in which the casing of the device appears partially sectioned in order to show clearly its internal structure, according to a preferred exemplary practical embodiment of the invention, in which the helicoidal groove is placed on the actual thread of the container and in which the casing includes a retention hook for said container.
Figure 2:
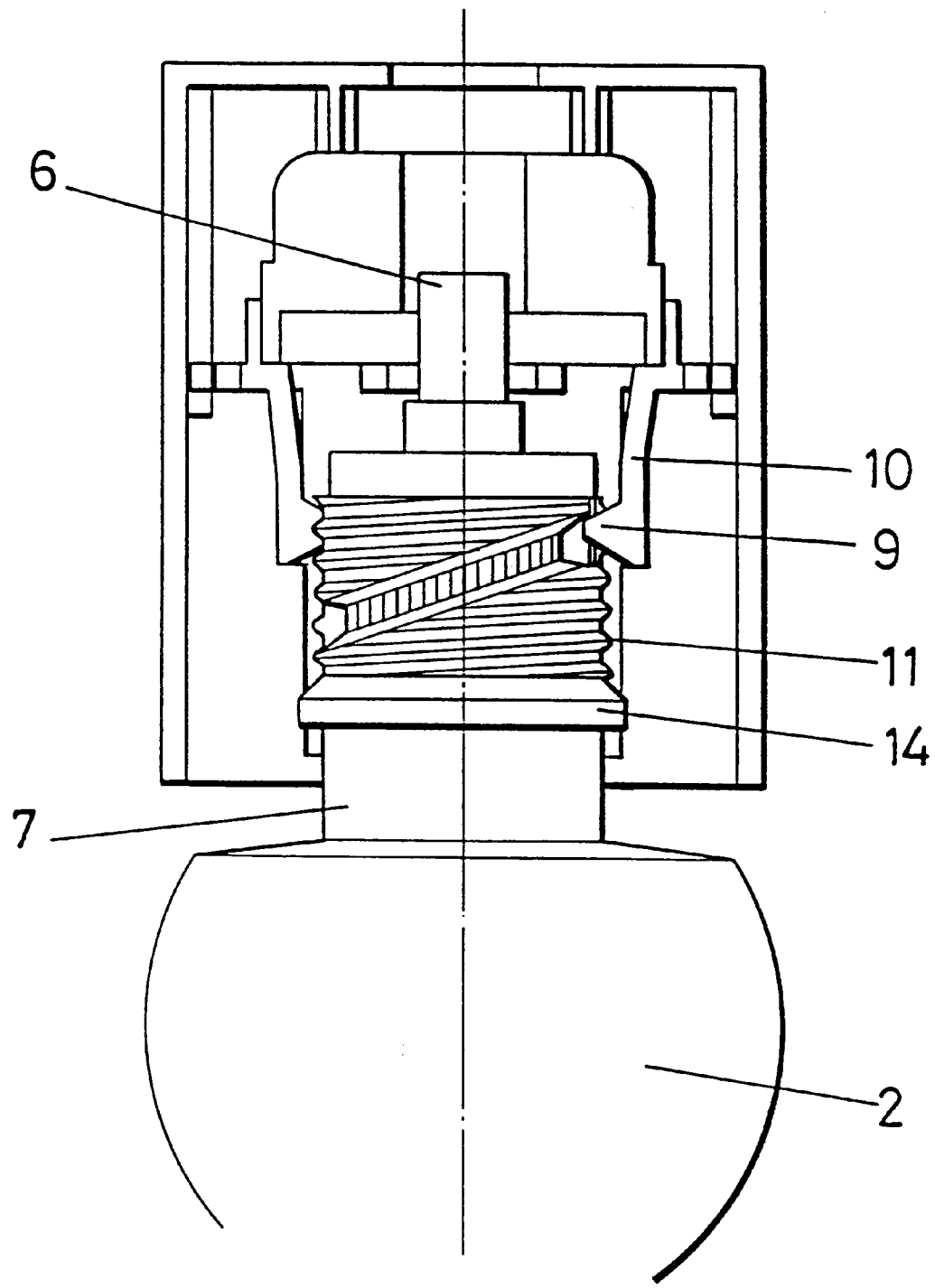
FIG. 2 shows another side elevational view of the assembly represented in the previous figure, with the same type of representation and with the device turned 90°.

In view of these figures and especially of FIGS. 1 through 5, it may be observed how in the device recommended, participate as any conventional device of this type, a casing (1), capable of receiving the container vessel (2) of the product dealt with, be it an environmental product or an insecticide product, said vessel which, as is also conventional, couples to the casing (1) generally by partial "plugging", said casing (1) being provided with a side extension (3) finished off with a plug socket (4), for connection to the electric supply network of a set of electroheating resistors (5), which in the present case are of the "PTC" type, advantageously established in the centre of the casing (1), and which also in the present case, are fixed, a wick (6) being established between the location area of said resistors (5) and the bottom of the vessel (2), said wick which, by capillarity, absorbs said product, making it rise towards the area of influence of the resistors (5).

Then, according to the essentiality of the invention, and as has just been pointed out, the electroheating resistors (5) are fixed, being established unmoveably in the centre of the casing (1), wick (6) being, together with the actual vessel (2), those which are axially displaceable in the centre of the casing (1), to penetrate the upper end of said wick (6) in greater or lesser degree, in the field of influence of the PTC'S (5).

For this and as has been especially observed in FIG. 1, the body of the vessel (2), which may adopt any configuration, presents at least one sector (7) of revolution, in which a helicoidal groove (8) is established, which determines a large pitch thread, in which at least one tooth (9) plays, which forms part of the casing (1) and preferably placed at the free end of an arm (10) which is elastically deformable, in such a manner that said tooth (9) acts as thread which causes the rapid axial advance in one or another direction of the vessel (2), and consequently of the upper end of the wick (6), when said vessel (2) is provided with a rotational movement, in one or another direction, through the end and lower sector of the same which projects as regards the casing (1), as is also observed in FIG. 1.

Figure 6:
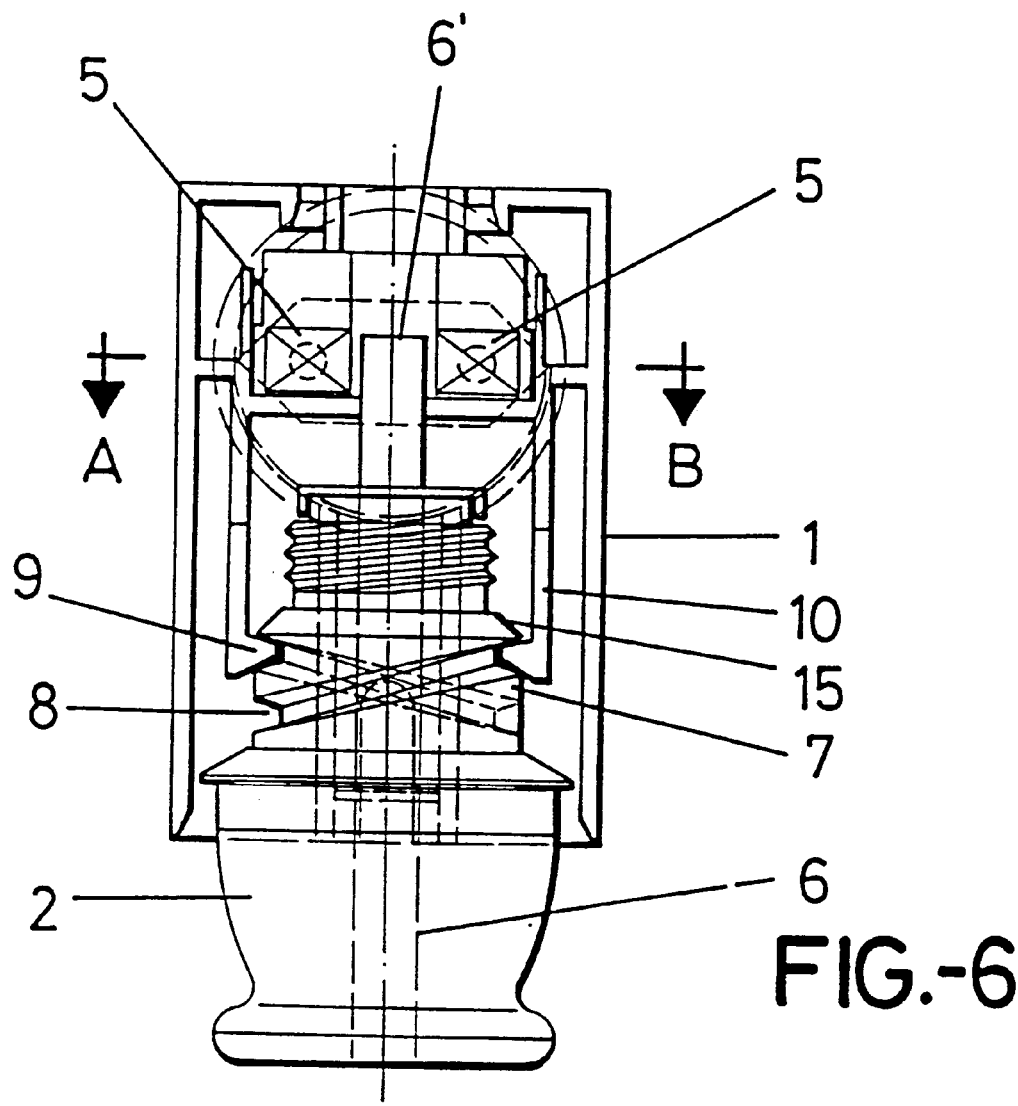
FIG. 6 shows a similar representation to that of FIG. 2 though corresponding to a practical embodiment in which the helicoidal groove is placed independently from the thread of the container.
Figure 7:
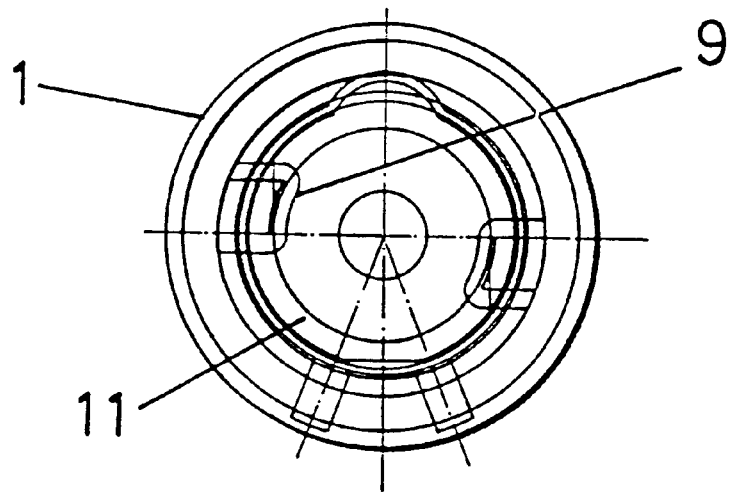
FIG. 7 shows a cross section of the assembly represented in the previous figure, according to the cut line A–B of said figure.
Figure 9:
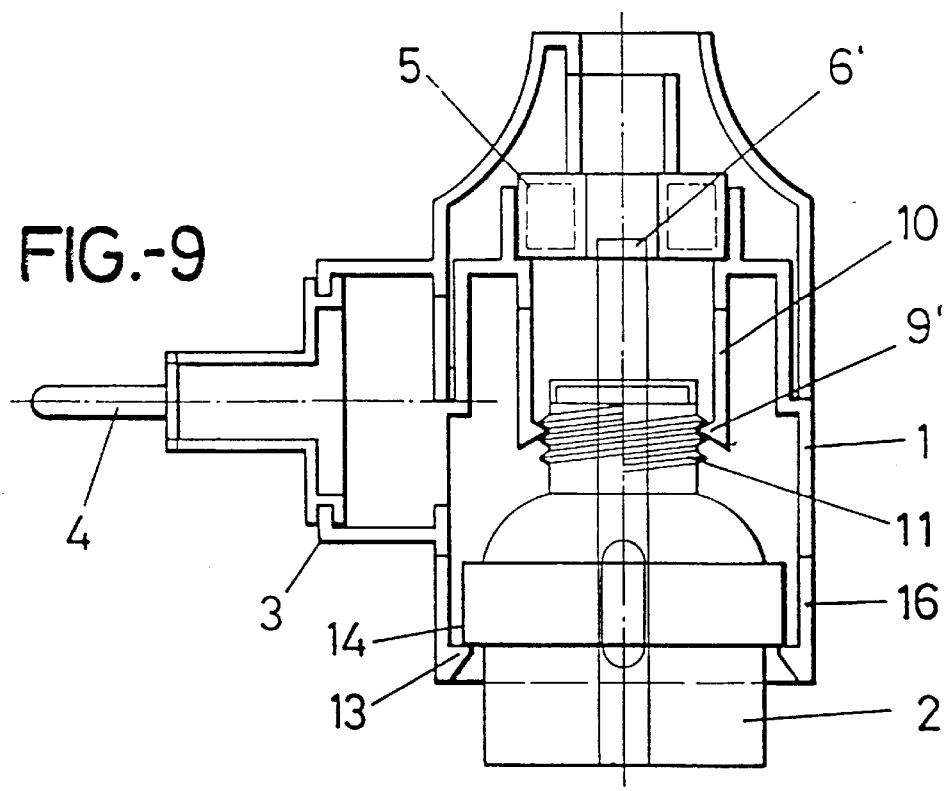
FIG. 9 finally shows a similar representation to that of FIG. 8, though with the casing sectioned and according to a practical embodiment variant in which the device uses the actual thread of the vessel, initially usable for the closing stopper of the same, as means of adjustment for the intensity of evaporation.

Specifically, in the exemplary practical embodiment of these FIGS. 1 through 5, the groove (8) is superposed to the actual thread (11) of the container (1) initially foreseen for the closing stopper of the same, though said groove may be independent from the thread (11), as happens in the exemplary practical embodiment represented in FIG. 6, or else it may be usable as groove of the actual thread (11) as in the case represented in FIG. 9, with the exception that in this case and as is obvious, the adjustment operation results to be slower since the thread pitch (11) is smaller than that of the groove (8), also having to adapt the tooth or teeth (9') to said thread (11) also with less depth than the groove (8).

Thanks to this simple operation, the upper end of the wick (6) is capable of remaining confronted to the electroheating resistors (5), or to adopt a lower position in which the thermal influence of said resistors is much less and in consequence, the intensity of the evaporation of the product dragged by the wick (6) from the interior of the bottle or vessel (2) is also less.

In order to avoid the total uncoupling of the container (2) during the adjustment operation, in this exemplary practical embodiment it has been provided, that on the casing (1), a hook (12) of tilting character is assembled, the end positions of which have been represented in continuous and discontinuous lines in FIG. 1, trigger which acts, by means of its retention tooth (13) on the stepping defined by a perimetral projection (14) operationally established in the container (2).

However, and according to the embodiment variant represented in FIG. 6, the groove (8) may present closed ends in such a manner, that it may act in a complementary way as rotation restricting stop both in one and another direction for the vessel (2) and in consequence, as stop which impossibilitates the accidental uncoupling of the vessel (2) as regards the casing (1).

In this case, for the assembly and disassembly of the vessel (2), in the ineludible operations of the replacement of the same, the elastic deformability of the arms (10) have been foreseen, in which the teeth (9) are placed, and especially the existence of conical fronts of said teeth, which are complementary of another conical front (15) established on that actual container (2), in the access zone immediate to the groove (8).

In the case represented in FIG. 9, in which the actual thread (11) of container (2) is used, previously used for the stopper, as groove for the axial displacement of the same, the possibility of closing the ends of said thread (11) does not exist, due to which the hook (12) of FIG. 1 may be used as retention means for the container (2), or else elastically deformable flaps (16), established on the mouth of the actual casing (1) and provided with the same retention teeth (13) which act on the same stepping defined by the projection (14) of the container (2).

Figure 8:
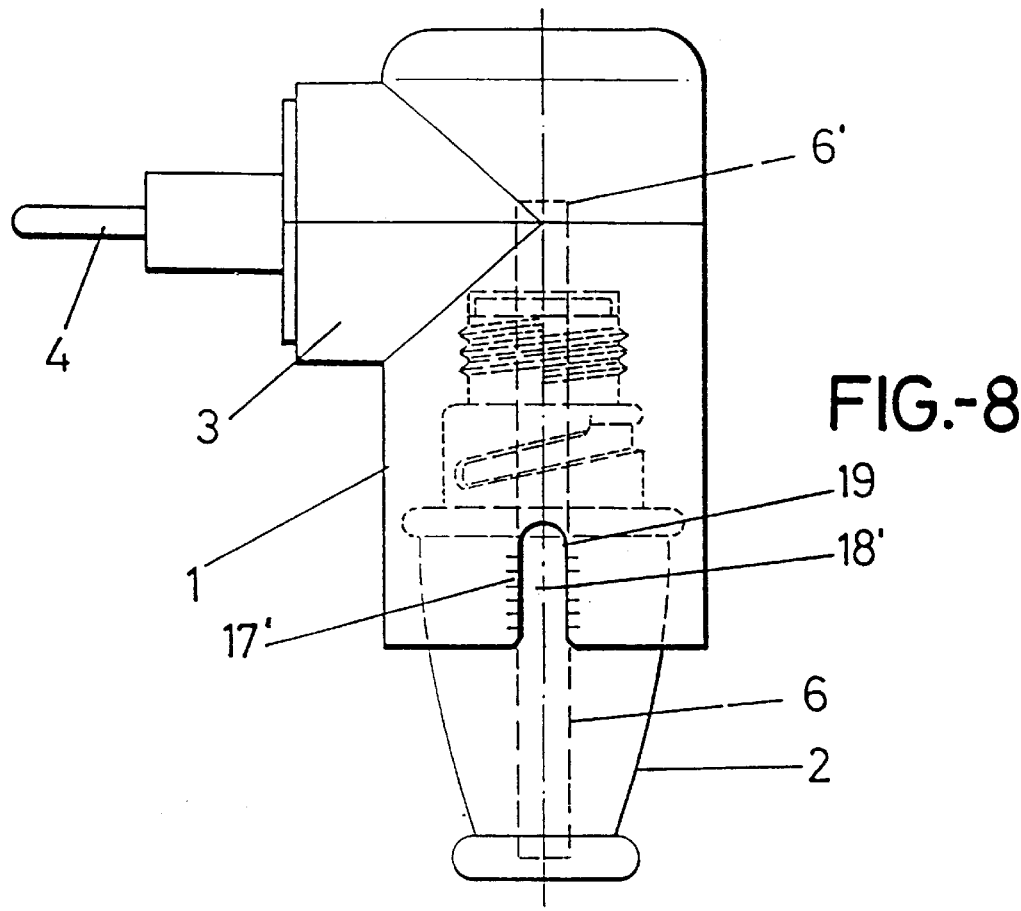
FIG. 8 shows a side elevational view of an assembly similar to that of FIG. 6, in which the configuration of the container varies and in which the casing of the device, without being sectioned, appears turned 90° as regards the position of FIG. 6.

Given that the intensity of evaporation depends on the relative positioning between the container (2), moveable, and the casing (1), fixed to the wall by means of the plug socket (4), in order to detect visually the level of intensity selected at each moment, it has been provided, according to the embodiment variant of the FIGS. 1 through 5, that the body (2) of the container, in its visible sector, be provided with a scale (17), moveable, which in the rotational movement of said container (2) changes its relative position as regards a fixed pointer (18) established on the casing. However, instead of detecting the angular position of the container (2), as in this embodiment, the axial position of the same may be used, as in the example represented in FIG. 8, in which case, the graded scale (17') is the one which is fixed, being placed on the actual casing (1), specifically on one or both sides of a deep vertical groove (19), in the centre of which, a circumferential mark (18') plays, established peripherically on the body (2) of the container, which shall obviously be displaced along the scale (17'), in one and another direction, when the body of the container (2) also turns in one or another direction.

What is claimed is:

1. An evaporator device for volatile products comprising:

a container vessel comprising a wick;

a casing comprising a central opening into which the wick is insertable, and heating means disposed in the casing for heating the wick with an intensity that varies depending on a position of the wick with respect to the heating means;

said vessel and casing collectively comprising groove and tooth means, including at least one helicoidal groove and a first tooth that moves along the groove upon an axial displacement of the vessel in said casing, for maintaining the wick in said casing in any of a plurality of positions with respect to said heating means, including a first position wherein an end of the wick is a first distance from the heating means and a second position wherein the end of the wick is a greater distance from the heating means such that the heating means heats the wick with a greater intensity with the wick disposed in the first position than in the second position.

2. The evaporator device as claimed in claim 1, wherein said tooth means comprises an elastically deformable arm connected to said casing, said first tooth being disposed at a free end of the arm.

3. The evaporator device as claimed in claim 2, wherein said device further comprises mounting means, comprising a projection on said vessel and a retention tooth in said casing, for mounting said vessel in the casing such that said vessel will not separate from said casing when said wick is displaced from said first position to said second position.

4. The evaporator device as claimed in claim 3, wherein said container vessel includes a neck comprising a threaded portion on its outer surface.

5. The evaporator device as claimed in claim 4, wherein said groove is superposed on said threaded portion of said neck.

6. The evaporator device as claimed in claim 5, wherein said heating means comprises a plurality of electroheating resistors and said casing includes a plug socket for feeding said resistors.

7. The evaporator device as claimed in claim 6, wherein said retention tooth engages said projection and is disposed on an elastically deformable flap connected to said casing.

8. The evaporator device as claimed in claim 6, wherein said retention tooth is part of a hook, said hook being manually displaceable within said casing so as to engage and disengage said projection.

9. The evaporator device as claimed in claim 7 comprising measuring means, including a graduated scale on the vessel and a fixed pointer on the casing, for measuring rotational movement of said vessel to detect an axial displacement of said wick.

10. The evaporator device as claimed in claim 7, wherein said casing includes a vertically elongated, wide notch at a lower portion of said casing, said notch includes a graduated scale, and said vessel has a perimetral mark, whereby an axial displacement of said wick can be measured with said mark in relation to said scale.

11. The evaporator device as claimed in claim 2, wherein said groove includes closed ends that restrict rotational movement of said container vessel.

12. The evaporator device as claimed in claim 2 comprising thread on a neck of said vessel, said thread comprising said at least one groove, said first tooth engaging said thread.

13. The evaporator device as claimed in claim 11, wherein said device further comprises mounting means, comprising a projection on said vessel and a retention tooth in said casing, for mounting said vessel in the casing such that said vessel will not separate from said casing when said wick is displaced from said first position to said second position.

14. The evaporator device as claimed in claim 13, wherein said heating means comprises a plurality of electroheating resistors and said casing includes a plug socket for feeding said resistors.

15. The evaporator device as claimed in claim 14, wherein said retention tooth engages said projection and is disposed on an elastically deformable flap connected to said casing.

16. The evaporator device as claimed in claim 14, wherein said retention tooth is part of a hook, said hook being manually displaceable within said casing so as to engage and disengage said projection.

17. The evaporator device as claimed in claim 15 comprising measuring means, including a graduated scale on the vessel and a fixed pointer on the casing for measuring rotational movement of said vessel to detect an axial displacement of said wick.

18. The evaporator device as claimed in claim 15, wherein said casing includes a vertically elongated, wide notch at a lower portion of said casing, said notch includes a graduated scale, and said vessel has a perimetral mark, whereby an axial displacement of said wick can be measured with said mark in relation to said scale.

* * * * *